Nov. 28, 1961 D. D. BELCHER Plant Pat. 2,107

BIRCH TREE

Original Filed Sept. 21, 1959

INVENTOR.
DARROLD D. BELCHER
BY
BUCKHORN, CHEATHAM & BLORE
ATTORNEYS

United States Patent Office

Plant Pat. 2,107
Patented Nov. 28, 1961

2,107
BIRCH TREE

Darrold D. Belcher, 210 SE. Vista Ave., Gresham, Oreg.

Continuation of abandoned application Ser. No. 841,424, Sept. 21, 1959. This application Sept. 19, 1960, Ser. No. 57,088

1 Claim. (Cl. 47—59)

The present invention relates to a new and distinct variety of birch tree, believed to be a seedling variant of the European white birch or *Betula pendula,* or *Betula pendula alba* as it is sometimes referred to. This application is a continuation of my prior application entitled Birch Tree, filed September 21, 1959, and bearing Serial No. 841,424, now abandoned.

Its primary distinguishing characteristic is its purple leaf coloring, similar to the purple leaf birch, *Betula pendula purpurea,* and the marked drooping of its main and side branches. This drooping can best be defined by comparison to other birches.

The seedling was found by me near Gresham, Oregon in a nursery containing many other trees, including European white birch but no purple leaf birch.

I have reproduced near Gresham, Oregon the new variety asexually, specifically by removing branches from trees of my invention and budding them onto European white birch, and removing the upper part of the old tree after it is known that the budding is successful. The characteristics of my tree have proved to be firmly fixed.

Figure 2:
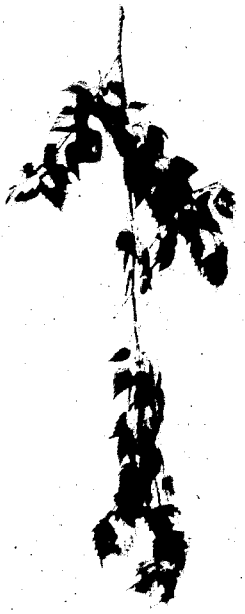
Figure 3:
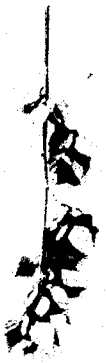
Figure 1:
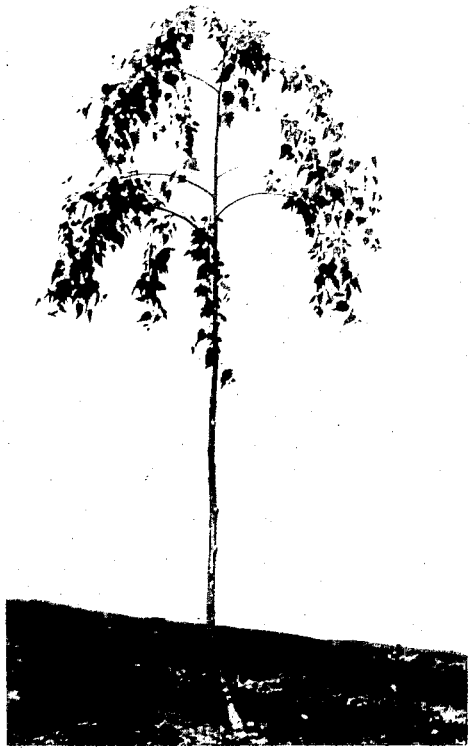

FIG. 1 is a photographic reproduction in color of a three-year-old tree of my invention, the lower branches having been removed from time to time for reproduction purposes, the color being as nearly true as is reasonably possible to make the same in a color illustration of this character;

FIG. 2 is a photographic reproduction in color on an enlarged scale of a branch of a tree of my invention, showing primarily the front surfaces of the leaves, the color being nearly as true as it is reasonably possible to make the same in a color illustration of this character, the color of FIG. 2 being more nearly true than that in FIG. 1; and FIG. 3 is a photographic reproduction in color of a branch of a tree of my invention, on the same scale as FIG. 2, but showing primarily the back surfaces of the leaves, the color being nearly as true as it is reasonably possible to make the same in a color illustration of this character.

The birch tree shown in FIG. 1 is a three-year-old tree.

In spite of the botanical name, *pendula,* it is well known that the *Betula pendula* does not develop any pendulous habit except for a distinct droop of only the outer branchlets toward mature age. The cutleaf European birch, *Betula pendula gracitis,* has drooping branchlets, but the main branches do not droop.

The *Betula pendula purpurea* has little drooping tendencies and in general the branches of this tree are upwardly inclined and relatively straight. The *Betula pendula youngii* is generally similar to the *Betula pendula alba* but has finer leaves. The *youngii* has weeping branchlets, but the main branches do not droop.

In contrast to the above, the branches of my tree display remarkable drooping even at an early age. For instance, in two-year-old trees, the main branches are distinctly arched commencing upwardly and arching outwardly and downwardly in many instances extending below the level of the base ends of the main branch. In a typical five feet, two-year-old tree of my invention the droop from the highest point of the arch of a main branch to the lowest leaf on the end of the main branch varied from around eight inches to around eighteen inches.

In a three-year-old tree as shown in FIG. 1, the drooping is even more marked than in a two-year-old tree, made apparent by a sharper bend in the branches as compared to that in a two-year-old tree.

In a five-year-old tree the drooping is even more marked. In many instances, the lower branches in a tree approximately eight feet tall drooped two to three feet, in some cases dragging or touching the ground.

The leaves of my birch tree are very similar to that of the purple birch; that is deltoid shaped with a relatively flat base, which is sometimes slightly cordate in older leaves. The margin of a leaf is distinctly double toothed, but not lobed or deeply notched as is the leaf of the cutleaf weeping birch.

The leaves in general vary from approximately 1 inch to 2 inches in length and from ⅞ inch to 1½ inches across near the leaf base.

The front surfaces of new growth leaves has a blackish, reddish purple color, rather oily in appearance, with reddish veins. The color does not appear in the Maerz and Paul Dictionary of Color, second edition, 1950, but approximates color L12 on Plate 48.

The back surfaces of new growth leaves are similar in color to the front, but without the oily appearance.

In old leaves, from the front, the veins still retain a reddish cast, though more subdued, and the leaves incorporate a dark green tinge. The color is not found in the above-mentioned dictionary, but approximates the color of blocks A6—A9 of Plate 24.

The back surfaces of old leaves assume a yellowish green cast, retaining a reddish tinge. The color is not found in the above-mentioned dictionary but approximates block J5 of Plate 16.

As the new growth gets older, and changes color, the bronze tinge becomes more apparent in the intermediate growth, and then becomes less apparent in old growth.

*Summary of new tree*

*Growth.*—Rapid and vigorous.

*Trunk.*—Straight, white bark around fourth or fifth year.

*Leaf color.*—Bronze-purple, like purple birch.

*Branches.*—Both main and side branches droop markedly with main branches distinctly arched.

I claim:

A new variety of birch tree substantially as herein shown and described, characterized particularly as to novelty by displaying early and marked drooping of the main branches, and having leaves which initially are of deep purple-bronze color, and gradually incorporate a deep green cast as the leaves grow older.

No references cited.